(12) United States Patent
Harvey et al.

(10) Patent No.: US 10,421,952 B1
(45) Date of Patent: ***Sep. 24, 2019

(54) MUTANT ORGANOPHOSPHORUS ACID ANHYDROLASE ENZYMES HAVING INCREASED CATALYTIC EFFICIENCY ON V-AGENTS

(71) Applicant: U.S. Army Edgewood Chemical Biological Center, APG, MD (US)

(72) Inventors: Steven P Harvey, Lutherville, MD (US); Mark A Guelta, White Marsh, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 45 days.

This patent is subject to a terminal disclaimer.

(21) Appl. No.: 15/883,331

(22) Filed: Jan. 30, 2018

(51) Int. Cl.
| | |
|---|---|
| *C12N 9/16* | (2006.01) |
| *A62D 3/02* | (2007.01) |
| *A61K 38/00* | (2006.01) |
| *A62D 101/26* | (2007.01) |
| *A62D 101/02* | (2007.01) |

(52) U.S. Cl.
CPC .............. *C12N 9/16* (2013.01); *A62D 3/02* (2013.01); *C12Y 301/08002* (2013.01); *A61K 38/00* (2013.01); *A62D 2101/02* (2013.01); *A62D 2101/26* (2013.01)

(58) Field of Classification Search
None
See application file for complete search history.

(56) References Cited

PUBLICATIONS

Cheng et al. (Applied and Environmental Microbiology, May 1996, p. 1636-1641).*

* cited by examiner

*Primary Examiner* — Suzanne M Noakes
*Assistant Examiner* — Jae W Lee
(74) *Attorney, Agent, or Firm* — Ulysses John Biffoni

(57) ABSTRACT

The invention is directed toward mutant, non-wild-type organophosphorus acid anhydrolases (OPPAs) having three or more site mutations, methods of production, kits and methods of use to effectively degrade toxic V-agent type chemical compounds such as VX, VR, CVX, and VM.

21 Claims, 2 Drawing Sheets
Specification includes a Sequence Listing.

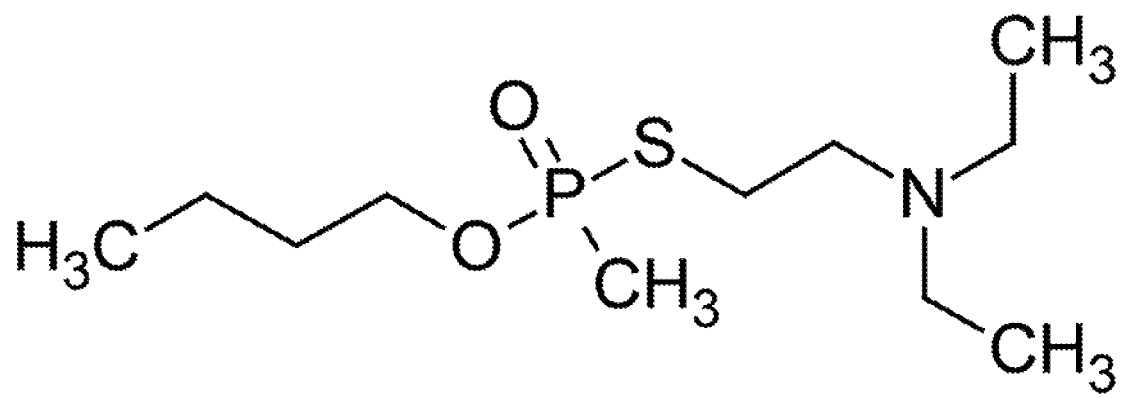
FIG. 3. CVX
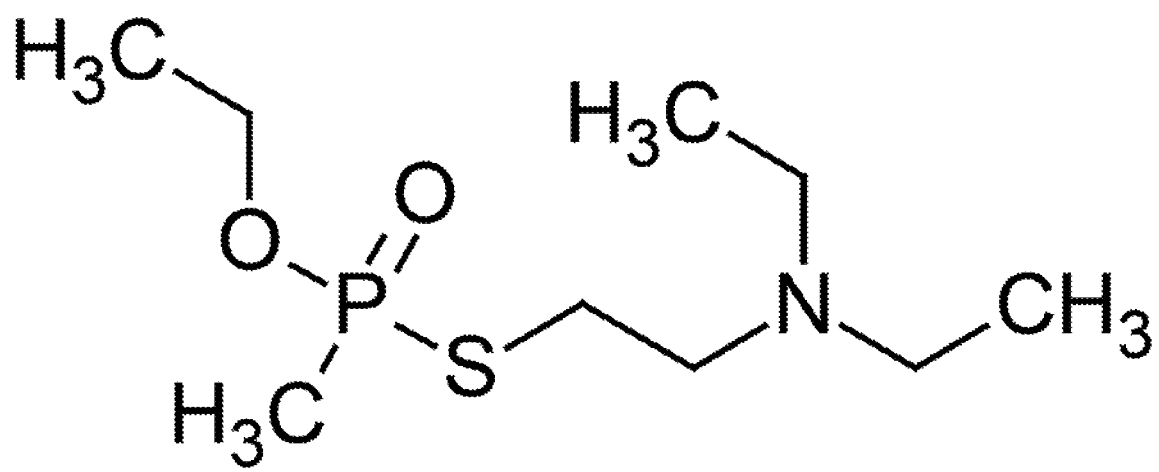
FIG. 4. VM

SEQUENCE LISTING

```
<160> NUMBER OF SEQ ID NOS: 4

<210> SEQ ID NO 1
<211> LENGTH: 440
<212> TYPE: PRT
<213> ORGANISM: Unknown
<220> FEATURE:
<223> OTHER INFORMATION: Wild-Type Organophosphorus Acid Anhydrolase

<400> SEQUENCE: 1

Met Asn Lys Leu Ala Val Leu Tyr Ala Glu His Ile Ala Thr Leu Gln
1               5                   10                  15

Lys Arg Thr Arg Glu Ile Ile Glu Arg Glu Asn Leu Asp Gly Val Val
            20                  25                  30
```

-continued

```
Phe His Ser Gly Gln Ala Lys Arg Gln Phe Leu Asp Met Tyr Tyr
         35                  40                  45
Pro Phe Lys Val Asn Pro Gln Phe Lys Ala Trp Leu Pro Val Ile Asp
 50                  55                  60
Asn Pro His Cys Trp Ile Val Ala Asn Gly Thr Asp Lys Pro Lys Leu
 65                  70                  75                  80
Ile Phe Tyr Arg Pro Val Asp Phe Trp His Lys Val Pro Asp Glu Pro
                 85                  90                  95
Asn Glu Tyr Trp Ala Asp Tyr Phe Asp Ile Glu Leu Leu Val Lys Pro
                100                 105                 110
Asp Gln Val Glu Lys Leu Leu Pro Tyr Asp Lys Ala Arg Phe Ala Tyr
                115                 120                 125
Ile Gly Glu Tyr Leu Glu Val Ala Gln Ala Leu Gly Phe Glu Leu Met
             130                 135                 140
Asn Pro Glu Pro Val Met Asn Phe Tyr His Tyr His Arg Ala Tyr Lys
145                 150                 155                 160
Thr Gln Tyr Glu Leu Ala Cys Met Arg Glu Ala Asn Lys Ile Ala Val
                 165                 170                 175
Gln Gly His Lys Ala Ala Arg Asp Ala Phe Phe Gln Gly Lys Ser Glu
             180                 185                 190
Phe Glu Ile Gln Gln Ala Tyr Leu Leu Ala Thr Gln His Ser Glu Asn
         195                 200                 205
Asp Thr Pro Tyr Gly Asn Ile Val Ala Leu Asn Glu Asn Cys Ala Ile
     210                 215                 220
Leu His Tyr Thr His Phe Asp Arg Val Ala Pro Ala Thr His Arg Ser
225                 230                 235                 240
Phe Leu Ile Asp Ala Gly Ala Asn Phe Asn Gly Tyr Ala Ala Asp Ile
                 245                 250                 255
Thr Arg Thr Tyr Asp Phe Thr Gly Glu Gly Glu Phe Ala Glu Leu Val
             260                 265                 270
Ala Thr Met Lys Gln His Gln Ile Ala Leu Cys Asn Gln Leu Ala Pro
         275                 280                 285
Gly Lys Leu Tyr Gly Glu Leu His Leu Asp Cys His Gln Arg Val Ala
     290                 295                 300
Gln Thr Leu Ser Asp Phe Asn Ile Val Asn Leu Ser Ala Asp Glu Ile
305                 310                 315                 320
Val Ala Lys Gly Ile Thr Ser Thr Phe Phe Pro His Gly Leu Gly His
                 325                 330                 335
His Ile Gly Leu Gln Val His Asp Val Gly Gly Phe Met Ala Asp Glu
             340                 345                 350
Gln Gly Ala His Gln Glu Pro Pro Glu Gly His Pro Phe Leu Arg Cys
         355                 360                 365
Thr Arg Lys Ile Glu Ala Asn Gln Val Phe Thr Ile Glu Pro Gly Leu
     370                 375                 380
Tyr Phe Ile Asp Ser Leu Leu Gly Pro Leu Ala Ala Thr Asp Asn Asn
385                 390                 395                 400
Gln His Ile Asn Trp Asp Lys Val Ala Glu Leu Lys Pro Phe Gly Gly
                 405                 410                 415
Ile Arg Ile Glu Asp Asn Ile Ile Val His Glu Asp Ser Leu Glu Asn
             420                 425                 430
Met Thr Arg Glu Leu Glu Leu Asp
         435                 440
```

<210> SEQ ID NO 2
<211> LENGTH: 440
<212> TYPE: PRT
<213> ORGANISM: Unknown
<220> FEATURE:
<223> OTHER INFORMATION: Non-Wild-Type FLYA Organophosphorus Acid
      Anhydrolase

<400> SEQUENCE: 2

Met Asn Lys Leu Ala Val Leu Tyr Ala Glu His Ile Ala Thr Leu Gln
1               5                   10                  15

Lys Arg Thr Arg Glu Ile Ile Glu Arg Glu Asn Leu Asp Gly Val Val
            20                  25                  30

Phe His Ser Gly Gln Ala Lys Arg Gln Phe Leu Asp Asp Met Tyr Tyr
        35                  40                  45

Pro Phe Lys Val Asn Pro Gln Phe Lys Ala Trp Leu Pro Val Ile Asp
    50                  55                  60

Asn Pro His Cys Trp Ile Val Ala Asn Gly Thr Asp Lys Pro Lys Leu
65                  70                  75                  80

Ile Phe Tyr Arg Pro Val Asp Phe Trp His Lys Val Pro Asp Glu Pro
                85                  90                  95

Asn Glu Tyr Trp Ala Asp Tyr Phe Asp Ile Glu Leu Leu Val Lys Pro
            100                 105                 110

Asp Gln Val Glu Lys Leu Leu Pro Tyr Asp Lys Ala Arg Phe Ala Tyr
        115                 120                 125

Ile Gly Glu Tyr Leu Glu Val Ala Gln Ala Leu Gly Phe Glu Leu Met
    130                 135                 140

Asn Pro Glu Pro Val Met Asn Phe Tyr His Tyr His Arg Ala Tyr Lys
145                 150                 155                 160

Thr Gln Tyr Glu Leu Ala Cys Met Arg Glu Ala Asn Lys Ile Ala Val
                165                 170                 175

Gln Gly His Lys Ala Ala Arg Asp Ala Phe Phe Gln Gly Lys Ser Glu
            180                 185                 190

Phe Glu Ile Gln Gln Ala Tyr Leu Leu Ala Thr Gln His Ser Glu Asn
        195                 200                 205

Asp Thr Pro Phe Gly Asn Tyr Val Ala Leu Asn Glu Asn Cys Ala Ile
    210                 215                 220

Leu His Tyr Thr His Phe Asp Arg Val Ala Pro Ala Thr His Arg Ser
225                 230                 235                 240

Phe Leu Ile Asp Ala Gly Ala Asn Phe Asn Gly Tyr Ala Ala Asp Ile
                245                 250                 255

Thr Arg Thr Tyr Asp Phe Thr Gly Glu Gly Glu Phe Ala Glu Leu Val
            260                 265                 270

Ala Thr Met Lys Gln His Gln Ile Ala Leu Cys Asn Gln Leu Ala Pro
        275                 280                 285

Gly Lys Leu Tyr Gly Glu Leu His Leu Asp Cys His Gln Arg Val Ala
    290                 295                 300

Gln Thr Leu Ser Asp Phe Asn Ile Val Asn Leu Ser Ala Asp Glu Ile
305                 310                 315                 320

Val Ala Lys Gly Ile Thr Ser Thr Phe Phe Pro His Gly Leu Gly His
                325                 330                 335

His Ile Gly Leu Gln Leu Ala Asp Val Gly Gly Phe Met Ala Asp Glu
            340                 345                 350

Gln Gly Ala His Gln Glu Pro Pro Glu Gly His Pro Phe Leu Arg Cys
        355                 360                 365

```
Thr Arg Lys Ile Glu Ala Asn Gln Val Phe Thr Ile Glu Pro Gly Leu
    370                 375                 380

Tyr Phe Ile Asp Ser Leu Leu Gly Pro Leu Ala Ala Thr Asp Asn Asn
385                 390                 395                 400

Gln His Ile Asn Trp Asp Lys Val Ala Glu Leu Lys Pro Phe Gly Gly
                405                 410                 415

Ile Arg Ile Glu Asp Asn Ile Ile Val His Glu Asp Ser Leu Glu Asn
            420                 425                 430

Met Thr Arg Glu Leu Glu Leu Asp
            435                 440

<210> SEQ ID NO 3
<211> LENGTH: 440
<212> TYPE: PRT
<213> ORGANISM: Unknown
<220> FEATURE:
<223> OTHER INFORMATION: Non-Wild-Type FLYG Organophosphorus Acid
      Anhydrolase

<400> SEQUENCE: 3

Met Asn Lys Leu Ala Val Leu T

```
Gly Lys Leu Tyr Gly Glu Leu His Leu Asp Cys His Gln Arg Val Ala
            290                 295                 300
Gln Thr Leu Ser Asp Phe Asn Ile Val Asn Leu Ser Ala Asp Glu Ile
305                 310                 315                 320
Val Ala Lys Gly Ile Thr Ser Thr Phe Phe Pro His Gly Leu Gly His
                325                 330                 335
His Ile Gly Leu Gln Leu Gly Asp Val Gly Gly Phe Met Ala Asp Glu
            340                 345                 350
Gln Gly Ala His Gln Glu Pro Pro Glu Gly His Pro Phe Leu Arg Cys
        355                 360                 365
Thr Arg Lys Ile Glu Ala Asn Gln Val Phe Thr Ile Glu Pro Gly Leu
    370                 375                 380
Tyr Phe Ile Asp Ser Leu Leu Gly Pro Leu Ala Ala Thr Asp Asn Asn
385                 390                 395                 400
Gln His Ile Asn Trp Asp Lys Val Ala Glu Leu Lys Pro Phe Gly Gly
                405                 410                 415
Ile Arg Ile Glu Asp Asn Ile Ile Val His Glu Asp Ser Leu Glu Asn
            420                 425                 430
Met Thr Arg Glu Leu Glu Leu Asp
        435                 440

<210> SEQ ID NO 4
<211> LENGTH: 440
<212> TYPE: PRT
<213> ORGANISM: Unknown
<220> FEATURE:
<223> OTHER INFORMATION: Non-Wild-Type FLYD-Q Organophosphorus Acid
      Anhydrolase

<400> SEQUENCE: 4

Met Asn Lys Leu Ala Val Leu Tyr Ala Glu His Ile Ala Thr Leu Gln
1

```
            195                 200                 205
Asp Thr Pro Phe Gly Asn Tyr Val Ala Leu Asn Glu Asn Cys Ala Ile
        210                 215                 220
Leu His Tyr Thr His Phe Asp Arg Val Ala Pro Ala Thr His Arg Ser
225                 230                 235                 240
Phe Leu Ile Asp Ala Gly Ala Asn Phe Asn Gly Tyr Ala Ala Asp Ile
            245                 250                 255
Thr Arg Thr Tyr Asp Phe Thr Gly Glu Gly Glu Phe Ala Glu Leu Val
            260                 265                 270
Ala Thr Met Lys Gln His Gln Ile Ala Leu Cys Asn Gln Leu Ala Pro
            275                 280                 285
Gly Lys Leu Tyr Gly Glu Leu His Leu Asp Cys His Gln Arg Val Ala
            290                 295                 300
Gln Thr Leu Ser Asp Phe Asn Ile Val Asn Leu Ser Ala Asp Glu Ile
305                 310                 315                 320
Val Ala Lys Gly Ile Thr Ser Thr Phe Phe Pro Gln Gly Leu Gly His
            325                 330                 335
His Ile Gly Leu Gln Leu Asp Asp Val Gly Gly Phe Met Ala Asp Glu
            340                 345                 350
Gln Gly Ala His Gln Glu Pro Pro Glu Gly Glu His Pro Phe Leu Arg Cys
            355                 360                 365
Thr Arg Lys Ile Glu Ala Asn Gln Val Phe Thr Ile Glu Pro Gly Leu
            370                 375                 380
Tyr Phe Ile Asp Ser Leu Leu Gly Pro Leu Ala Ala Thr Asp Asn Asn
385                 390                 395                 400
Gln His Ile Asn Trp Asp Lys Val Ala Glu Leu Lys Pro Phe Gly Gly
                405                 410                 415
Ile Arg Ile Glu Asp Asn Ile Ile Val His Glu Asp Ser Leu Glu Asn
            420                 425                 430
Met Thr Arg Glu Leu Glu Leu Asp
            435                 440
```

US 10,421,952 B1

MUTANT ORGANOPHOSPHORUS ACID ANHYDROLASE ENZYMES HAVING INCREASED CATALYTIC EFFICIENCY ON V-AGENTS

GOVERNMENT INTEREST

The invention described herein may be manufactured, used, and licensed by or for the United States Government.

FIELD OF THE INVENTION

The invention relates to novel enzymes that degrade one or more toxic chemical compounds. More specifically, the invention is related to organophosphorus acid anhydrolase mutants capable of degrading persistent chemical warfare V-type agents and other organophosphorus compounds such as pesticides and chemical nerve agents.

BACKGROUND OF THE INVENTION

A number of organophosphorus ("OP") compounds used by the agriculture industry and the military are highly toxic and thus hazardous to human health and harmful to the environment. For example, acetylcholinesterase-inhibiting OP compounds comprise the active ingredient of pesticides such as paraoxon as well as G-type nerve agents such as Sarin and Soman, etc., developed for chemical warfare. Thus, it is very important to be able to detoxify such OP compounds and to decontaminate surfaces and substances contaminated with these compounds.

One approach being investigated as a potential solution to this problem is enzyme-mediated detoxification. For example, a class of enzymes known as organophosphorus acid ("OPA") anhydrolases ("OPAA") (EC 3.1.8.2) can catalyze the hydrolysis of a variety of OP compounds, including pesticides and fluorinated "G-type" nerve agents, and such anhydrolases have been known to be produced via overexpression within the recombinant organism (see U.S. Pat. No. 5,928,927 to Cheng et al. incorporated herein by reference).

One family of organophosphorus compounds known as V-agents are particularly toxic and persistent. For example, ((Ethyl {2-[bis(propan-2-yl)amino]ethyl}sulfanyl) (methyl) phosphinate, known as VX, is very toxic to humans. The median lethal dose ($LD_{50}$) for humans is estimated to be about 10 milligrams when contact is through skin. The estimated $LC_{t50}$ for inhalation is estimated to be 30-50 mg min/m$^3$. The native OPAA enzyme has been described to possess catalytic activity against various chemical nerve agents, but its activity against the particularly toxic and persistent V-agents such as VX (Ethyl ({2-[bis(propan-2-yl) amino]ethyl}sulfanylmethyl)phosphinate) and others is only marginally detectable, and therefore, not practically useful as a decontaminant or as a medical countermeasure for VX poisoning.

In addition to VX, other V-agents of interest include VR (Russian VX) N,N-diethyl-2-(methyl-(2-methylpropoxy) phosphoryl)sulfanylethanamine); CVX (Chinese VX) S-[2-(Diethylamino)ethyl] O-n-butyl methylphosphonothioate); and agent VM (S-[2-(Diethylamino)ethyl] O-ethyl methylphosphonothioate).

Methods of producing organophosphorus acid anhydrolases for detoxifying organophosphorus compounds are well known in the art.

U.S. Pat. No. 5,928,927 to Cheng et al. teaches expression and composition comprising wild-type organophosphorus acid anhydrolases ("OPAA-2") from the *Alteromonus* sp. bacteria strain JD6.5.

U.S. 2013/0071394 to Troyer et al. teaches compositions and combinations containing an organophosphorus bioscavenger and a hyaluronan-degrading enzyme that can be used to treat or prevent organophosphorus poisoning, including nerve agent poisoning and pesticide poisoning. However, the bioscavenger that Troyer utilizes is also a wild-type OPAA.

U.S. Pat. No. 9,017,982 to Shah et al. teaches a non-wild-type organophosphorus acid anhydrolases having an amino acid substitution at position 212, such that the mutated OPAA may degrade (ethyl {2-[bis(propan-2-yl)amino] ethyl}sulfanyl) (methyl)phosphinate and other V-agents. However, the mutation occurs only at position 212 and the catalytic activity is only about 2-fold or less on VX, as compared to the wild-type OPAA. Therefore, new compounds and methods to effectively detoxify VX are needed.

SUMMARY OF THE INVENTION

The invention is directed towards mutant, non-wild type organophosphorus acid anhydrolase ("OPAA") enzymes that include a mutation at each of sequence positions 212, 215, 342, and 343 of SEQ ID NO: 1. In addition, in another embodiment the mutant OPAA includes an additional mutation at sequence position 332 of SEQ ID NO:1. The wild-type amino acid Tyrosine at position 212 of SEQ ID NO: 1 is substituted with an amino acid selected from the group consisting of Glycine (G), Phenylalanine (F), Proline (P), Glutamine (Q), and Threonine (T). The wild-type amino acid Isoleucine (I) at position 215 of SEQ ID NO: 1 is substituted with an amino acid selected from the group consisting of Tyrosine (Y), Leucine (L), Valine (V), Glutamine (Q), Proline (P), and Phenylalanine (F). The wild-type amino acid Valine (V) at position 342 of SEQ ID NO: 1 is substituted with an amino acid selected from the group consisting of Leucine (L), Threonine (T), Cysteine (C), Arginine (R), and Histidine (H). The wild-type amino acid Histidine (H) at position 343 of SEQ ID NO: 1 is substituted with an amino acid selected from the group consisting of Alanine (A), Glycine (G), and Aspartate (D). The wild-type amino acid Histidine (H) at position 332 may be substituted with the amino acid Glutamine (Q).

In one embodiment, the non-wild-type mutant OPPA has the sequence of SEQ ID NO: 2, or a catalytically active fragment thereof, having the specific mutations Y212F/V342L/I215Y/H343A (abbreviated FLYA). In another embodiment, the mutant OPAA has the sequence of SEQ ID NO: 3, or a catalytically active fragment thereof, having the specific mutations Y212F/V342L/I215Y/H343G (abbreviated FLYG). In another embodiment, the mutant OPPA has the sequence of SEQ ID NO: 4, or a catalytically active fragment thereof, having the specific mutations Y212F/V342L/I215Y/H343D/H332Q (abbreviated FLYD-Q). The mutant OPAA enzyme FLYA (SEQ ID NO: 2) exhibits a 33-fold increase in catalytic efficiency on VR and an 11-fold increase in catalytic efficiency on VX. The mutant OPAA enzyme FLYG (SEQ ID NO: 3) exhibits a 20-fold increase in catalytic efficiency on VR, an 18-fold increase in catalytic efficiency on VX, and a 5-fold increased catalytic efficiency on CVX. The mutant OPAA enzyme FLYD-Q (SEQ ID NO: 4) exhibits a 16-fold increase in catalytic efficiency on VM and a 2-fold increase in catalytic efficiency on CVX.

Also provided are kits and methods for catalytically degrading V-agents, for example, by contacting V-agents with the inventive mutant, non-wild-type organophosphorus acid anhydrolase proteins.

BRIEF DESCRIPTION OF THE DRAWINGS

The invention, together with other objects, features, aspects and advantages thereof will be more clearly understood from the following in conjunction with the accompanying drawings.

Figures 1, 2:
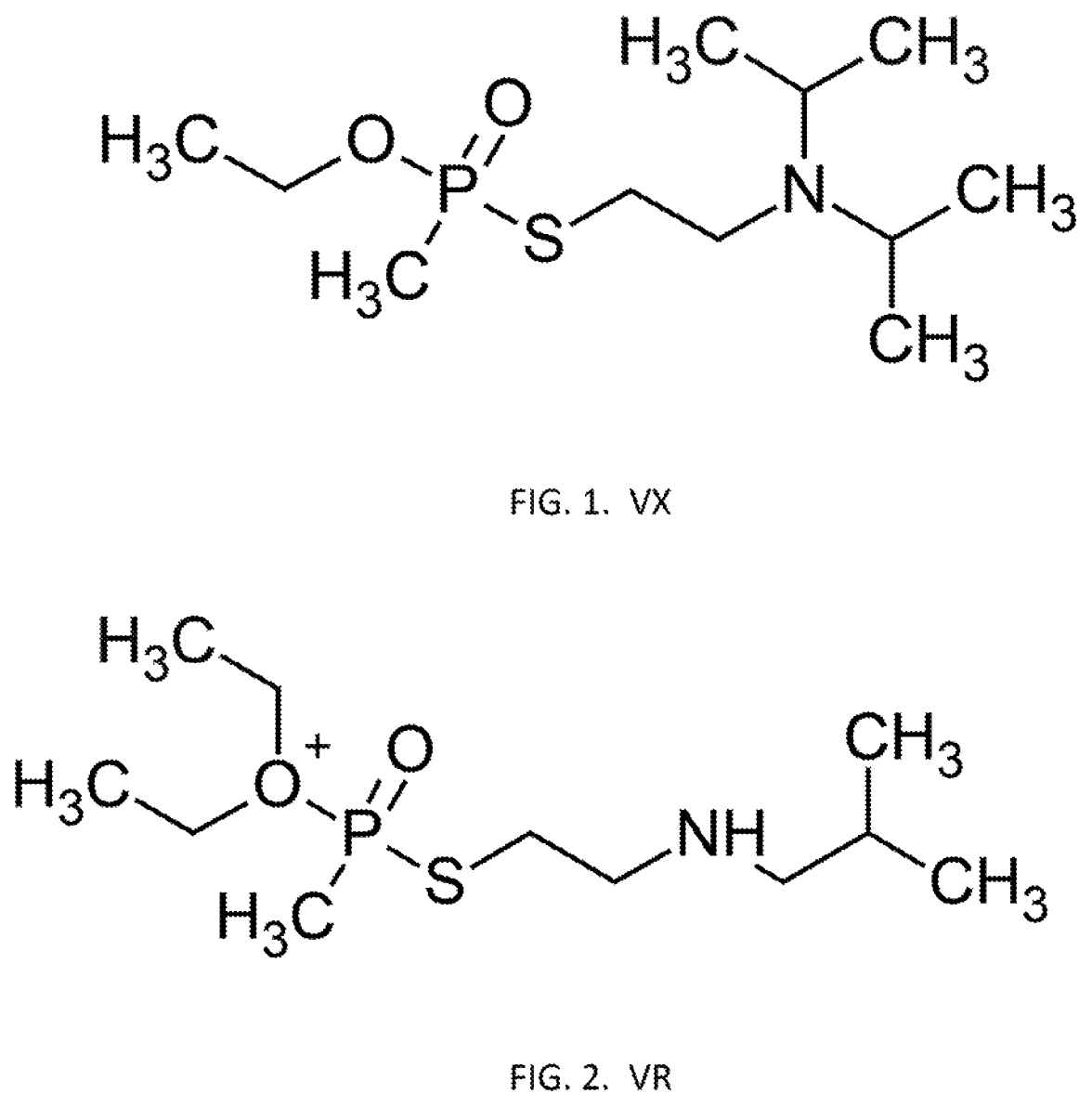

FIG. 1 illustrates the structure of nerve agent VX, (ethyl {2-[bis(propan-2-yl)amino]ethyl}sulfanyl)(methyl)phosphinate.

FIG. 2 illustrates the structure of nerve agent VR, N,N-diethyl-2-(methyl-(2-methylpropoxy)phosphoryl)sulfanylethanamine.

FIG. 3 illustrates the structure of nerve agent CVX, (S-[2-(Diethylamino)ethyl] O-n-butyl methylphosphonothioate).

FIG. 4 illustrates the structure of nerve agent VM, (S-[2-(Diethylamino)ethyl]O-ethyl methylphosphonothioate).

DETAILED DESCRIPTION OF THE EMBODIMENTS OF THE INVENTION

Native OPAA was originally derived from the bacterium *Alteromonas* sp. JD6.5 and its gene has subsequently been cloned into *E. coli*. The native OPAA enzyme has been described to possess catalytic activity against various chemical nerve agents but no activity against the particularly toxic and persistent agent VX was ever observed. Native OPAA has the amino acid sequence of:

```
                                              (SEQ ID NO: 1)
    1      MNKLAVLYAE HIATLQKRTR EIIERENLDG
           VVFHSGQAKR QFLDDMYPF

51      KVNPQFKAWL PVIDNPHCWI VANGTDKPKL
           IFYRPVDFWH KVPDEPNEYW

101      ADYFDIELLV KPDQVEKLLP YDKARFAYIG
           EYLEVAQALG FELMNPEPVM

151      NFYHYHRAYK TQYELACMRE ANKIAVQGHK
           AARDAFFQGY SEFEIQQAYL

201      LATQHSENDT PYGNIVALNE NCAILHYTHF
           DRVAPATHRS PLIDAGANFN

251      GYAADITRTY DFTGEGEFAE LVATMKQHQI
           ALCNQLAPGK LYGELHLDCH

301      QRVAQTLSDF NIVNLSADEI VAKGITSTFF
           PHGLGHHIGL QVHDVGGFMA

351      DEQGAHQEPP EGHPFLRCTR KIEANQVFTI
           EPGLYFIDSL LGDLAATDNN

401      QHINWDKVAE LKPFGGIRIE DNIIVHEDSL
           ENMTRELELD
```

The inventors have found that OPAAs having mutations at each of positions 212, 342, 215, and 343 of SEQ ID NO: 1 effectively catalyze VX, VR and CVX. A mutant, non-wild type organophosphorus acid anhydrolase protein particularly effective in catalyzing VX and VR preferably has the sequence of SEQ ID NO: 2, or a catalytically active fragment thereof, which is Y212F/V342L/I215Y/H343A (abbreviated FLYA). Another mutant, non-wild type organophosphorus acid anhydrolase protein particularly effective in catalyzing VX, VR, and CVX preferably has the sequence of SEQ ID NO: 3, or a catalytically active fragment thereof, which is Y212F/V342L/I215Y/H343G (abbreviated FLYG). Another mutant, non-wild type organophosphorus acid anhydrolase protein particularly effective in catalyzing VM and CVX preferably has the sequence of SEQ ID NO: 4, or a catalytically active fragment thereof, which is Y212F/V342L/I215Y/H343D/H332Q (abbreviated FLYD-Q).

The isolated mutant OPAA enzyme may be useful for in vivo treatment of VX poisoning, or for the catalytic decontamination of VX from surfaces or in the environment.

In one embodiment, the inventive, mutant non-wild-type OPAA enzyme (FLYA) has a sequence of:

```
                                              (SEQ ID NO: 2)
    1      MNKLAVLYAE HIATLQKRTR EIIERENLDG
           VVFHSGQAKR QFLDDMYPF

51      KVNPQFKAWL PVIDNPHCWI VANGTDKPKL
           IFYRPVDFWH KVPDEPNEYW

101      ADYFDIELLV KPDQVEKLLP YDKARFAYIG
           EYLEVAQALG FELMNPEPVM

151      NFYHYHRAYK TQYELACMRE ANKIAVQGHK
           AARDAFFQGY SEFEIQQAYL

201      LATQHSENDT PYGNIVALNE NCAILHYTHF
           DRVAPATHRS PLIDAGANFN

251      GYAADITRTY DFTGEGEFAE LVATMKQHQI
           ALCNQLAPGK LYGELHLDCH

301      QRVAQTLSDF NIVNLSADEI VAKGITSTFF
           PHGLGHHIGL QVHDVGGFMA

351      DEQGAHQEPP EGHPFLRCTR KIEANQVFTI
           EPGLYFIDSL LGDLAATDNN

401      QHINWDKVAE LKPFGGIRIE DNIIVHEDSL
           ENMTRELELD
```

In another embodiment, the inventive, mutant non-wild-type OPAA (FLYG) has a sequence of:

```
                                              (SEQ ID NO: 3)
    1      MNKLAVLYAE HIATLQKRTR EIIERENLDG
           VVFHSGQAKR QFLDDMYPF

51      KVNPQFKAWL PVIDNPHCWI VANGTDKPKL
           IFYRPVDFWH KVPDEPNEYW

101      ADYFDIELLV KPDQVEKLLP YDKARFAYIG
           EYLEVAQALG FELMNPEPVM

151      NFYHYHRAYK TQYELACMRE ANKIAVQGHK
           AARDAFFQGY SEFEIQQAYL

201      LATQHSENDT PYGNIVALNE NCAILHYTHF
           DRVAPATHRS PLIDAGANFN

251      GYAADITRTY DFTGEGEFAE LVATMKQHQI
           ALCNQLAPGK LYGELHLDCH

301      QRVAQTLSDF NIVNLSADEI VAKGITSTFF
           PHGLGHHIGL QVHDVGGFMA

351      DEQGAHQEPP EGHPFLRCTR KIEANQVFTI
           EPGLYFIDSL LGDLAATDNN

401      QHINWDKVAE LKPFGGIRIE DNIIVHEDSL
           ENMTRELELD
```

In another embodiment, the inventive, mutant non-wild-type OPAA (FLYD-Q) has a sequence of:

```
                                              (SEQ ID NO: 4)
  1    MNKLAVLYAE HIATLQKRTR EIIERENLDG
       VVFHSGQAKR QFLDDMYPF

51    KVNPQFKAWL PVIDNPHCWI VANGTDKPKL
       IFYRPVDFWH KVPDEPNEYW

101    ADYFDIELLV KPDQVEKLLP YDKARFAYIG
       EYLEVAQALG FELMNPEPVM

151    NFYHYHRAYK TQYELACMRE ANKIAVQGHK
       AARDAFFQGY SEFEIQQAYL

201    LATQHSENDT PYGNIVALNE NCAILHYTHF
       DRVAPATHRS PLIDAGANFN

251    GYAADITRTY DFTGEGEFAE LVATMKQHQI
       ALCNQLAPGK LYGELHLDCH

301    QRVAQTLSDF NIVNLSADEI VAKGITSTFF
       PHGLGHHIGL QVHDVGGFMA

351    DEQGAHQEPP EGHPFLRCTR KIEANQVFTI
       EPGLYFIDSL LGDLAATDNN

401    QHINWDKVAE LKPFGGIRIE DNIIVHEDSL
       ENMTRELELD
```

Alternatively, the non-wild-type OPAA may include 2, 3, 4, 5, 6, 7, 8, 9 or more non-wild-type amino acid residues located at positions other than positions 212, 215 and 342.

The non-wild-type OPAA may have additional non-wild-type amino acid substitutions, including but not limited to a deletion, or an additional amino acid sequence contained within the non-wild-type OPAA sequence.

In some embodiments, the non-wild-type OPAA is a fragment of wild-type OPAA wherein the fragment includes sufficient residues of OPAA to enable the mutated OPAA to be as functional and active as a wild-type OPAA, yet catalytically breakdown V-type agents at high efficiency. Preferably, the non-wild-type OPAA is of 617 AA in length, more preferably, the non-wild-type OPAA is of 500 AA in length, and most preferably, the non-wild-type OPAA is of 440 AA in length.

Amino acids present in the non-wild-type OPAA include the common amino acids alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine as well as less common naturally occurring amino acids, modified amino acids or synthetic compounds, such as alpha-asparagine, 2-aminobutanoic acid or 2-aminobutyric acid, 4-aminobutyric acid, 2-aminocapric acid (2-aminodecanoic acid), 6-aminocaproic acid, alpha-glutamine, 2-aminoheptanoic acid, 6-aminohexanoic acid, alpha-aminoisobutyric acid (2-aminoalanine), 3-aminoisobutyric acid, beta-alanine, allo-hydroxylysine, allo-sioleucine, 4-amino-7-methylheptanoic acid, 4-amino-5-phenylpentanoic acid, 2-aminopimelic acid, gamma-amino-beta-hydroxybenzenepentanoic acid, 2-aminosuberic acid, 2-carboxyazetidine, beta-alanine, beta-aspartic acid, biphenylalanine, 3,6-diaminohexanoic acid, butanoic acid, cyclobutyl alanine, cyclohexylalanine, cydohexylglycine, N5-aminocarbonylomithine, cyclopentyl alanine, cyclopropyl alanine, 3-sulfoalanine, 2,4-diaminobutanoic acid, diaminopropionic acid, 2,4-diaminobutyric acid, diphenyl alanine, NN-dimethylglycine, diaminopimelic acid, 2,3-diaminopropanoic acid, S-ethyithiocysteine, N-ethylasparagine, N-ethylglycine, 4-aza-phenylalanine, 4-fluoro-phenylalanine, gamma-glutamic acid, gamma-carboxyglutamic acid, hydroxyacetic acid, pyroglutamic acid, homoarginine, homocysteic acid, homocysteine, homohistidine, 2-hydroxyisovaleric acid, homophenylalanine, homoleucine, homoproline, homoserine, homoserine, 2-hydroxypentanoic acid, 5-hydroxylysine, 4-hydroxyproline, 2-carboxyoctahydroindole, 3-carboxyisoquinoline, isovaline, 2-hydroxypropanoic acid (lactic acid), mercaptoacetic acid, mercaptobutanoic acid, sarcosine, 4-methyl-3-hydroxyproline, mercaptopropanoic acid, norleucine, nipecotic acid, nortyrosine, norvaline, omega-amino acid, omithine, penicillamine (3-mercaptovaline), 2-phenylglycine, 2-carboxypiperidine, sarcosine (N-methylglycine), 2-amino-3-(4-sulfophenyl)propionic acid, 1-amino-1-carboxycyclopentane, 3-thienylalanine, epsilon-N-trimethyllysine, 3-thiazolylalanine, thiazolidine 4-carboxylic acid, alpha-amino-2,4-dioxopyrimidinepropanoic acid, and 2-naphthylalanine.

Modifications and changes can be made in the structure of the inventive non-wild-type OPAA that are the subject of the application and still obtain a molecule having similar or improved characteristics as the Y212F/V342L/I215Y/H343A (FLYA), Y212F/V342L/I215Y/H343G (FLYG), and Y212F/V342L/I215Y/H343D/H332Q (FLYD-Q) mutation sequence (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like or improved properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In making such changes, the substitution of amino acids whose hydropathic indices are preferably within ±2, more preferably within ±1, and most preferably within ±0.5.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5);

tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are preferably within ±2, more preferably within ±1, and most preferably within ±0.5.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gin: Asn), (Glu: Asp), (Gly: ala), (His: Asn, Gin), (ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of polypeptides can include variants having about 50%, 69%, 70%, preferably 80%, 90%, and 95% sequence identity to the protein of SEQ ID NO: 1.

It is appreciated that amino acids are optionally L- or D-isomers. The inventive non-wild-type OPAA may include mixtures of L- and D-isomers.

Without wish to be bound by theory, the OPAA enzyme has a substrate-binding site for chemicals. The substrate-binding site is composed of a small pocket, a large pocket, and a leaving group pocket. The large pocket is formed by Leu225, His226, His332, and Arg418. The leaving group pocket is composed of Tyr292 and Leu366. The small pocket is formed by residues Tyr212, Val342, His343, and Asp45 from the N-terminal domain of the opposite subunit in the dimer. All three pockets are in close proximity to the binuclear active site. It has been found for the present invention that modification for sites located within the small pockets of the OPAA, particularly 212, 215, 342, and 343 of SEQ ID NO: 1, imparts good binding and excellent catalytic activity on V-agents such as VX as shown in Tables 1-7, by effectively cleaving the P—S bonds of the V-type agents.

Method of Production

The non-wild-type OPAA is obtained by any of various methods known in the art illustratively including isolation from a cell or organism, chemical synthesis, expression of a nucleic acid sequence, and partial hydrolysis of larger OPAA sequences. Chemical methods of peptide synthesis are known in the art and include solid phase peptide synthesis and solution phase peptide synthesis or by the method of Hackeng, T M, et al., *Proc Natl Aced Sci USA*, 1997; 94(15):7845-50 or those reviewed by Miranda, L P, *Peptide Science*, 2000, 55:217-26 and Kochendoerfer G, *Curr Opin Drug Discov Devel*. 2001; 4(2):205-14. In some embodiments, the polypeptide sequences are chemically synthesized by Fmoc synthesis.

Alternatively, synthesis and expression of the non-wild-type OPAA is illustratively accomplished from transcription of a nucleic acid sequence encoding a peptide of the invention, and translation of RNA transcribed from nucleic acid sequence, modifications thereof, or fragments thereof. Protein expression is optionally performed in a cell based system such as in *E. coli*, Hela cells, or Chinese hamster ovary cells. It is appreciated that cell-free expression systems are similarly operable.

Further aspects of the present disclosure concern the purification, and in particular embodiments, the substantial purification, of a non-wild-type OPAA protein. The term "purified" or "isolated" as used herein, is intended to refer to a composition, isolatable from other components, wherein the non-wild-type OPAA is purified to any degree relative to its naturally-obtainable state. A purified non-wild-type OPAA, therefore, also refers to a non-wild-type OPAA free from the environment in which it may naturally occur.

Generally, "purified" or "isolated" will refer to a non-wild-type OPAA composition that has been subjected to fractionation to remove various other components, and which composition substantially retains its expressed biological activity. Where the term "substantially" purified is used, this designation will refer to a composition in which the protein or peptide forms the major component of the composition, such as constituting about 50% or more of the proteins in the composition.

Various methods for quantifying the degree of purification of a protein are known to those of skill in the art in light of the present disclosure as based on knowledge in the art. These include, for example, determining the specific activity of an active fraction, or assessing the number of peptides within a fraction by SDS/PAGE analysis. An illustrative method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

Various techniques suitable for use in peptide purification will be well known to those of skill in the art. These include, for example, precipitation with ammonium sulfate, polyethylene glycol, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein.

Additional methods of protein isolation illustratively include column chromatography, affinity chromatography, gel electrophoresis, filtration, or other methods known in the art. In some embodiments, a non-wild-type OPAA is expressed with a tag operable for affinity purification. An illustrative tag is a 6× His tag. A 6× His tagged inventive protein is illustratively purified by Ni-NTA column chromatography or using an anti-6× His tag antibody fused to a solid support. (Geneway Biotech, San Diego, Calif.) Other tags and purification systems are similarly operable.

It is appreciated that an inventive protein is not tagged. In this embodiment and other embodiments purification may be achieved by methods known in the art illustratively including ion-exchange chromatography, affinity chromatography using antibodies directed to the peptide sequence of interest, precipitation with salt such as ammonium sulfate, streptomycin sulfate, or protamine sulfate, reverse chromatography, size exclusion chromatography such as gel exclusion chromatography, HPLC, immobilized metal chelate chromatography, or other methods known in the art. One of skill in the art may select the most appropriate isolation and purification techniques without departing from the scope of this invention.

There is no general requirement that the non-wild-type OPAA always be provided in its most purified state. It is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater-fold purification than the same technique utilizing a low pressure chromatography system. Methods exhibiting a lower degree of relative purification may have advantages in total recovery of protein product, or in maintaining the activity of an expressed protein.

It is known that the migration of a protein can vary, sometimes significantly, with different conditions of SDS/PAGE (Capaldi et al., Biochem. Biophys. Res. Comm., 76:425, 1977). It will, therefore, be appreciated that under differing electrophoresis conditions, the apparent molecular weights of purified or partially purified expression products may vary.

Non-wild-type OPAA proteins or peptides of this invention may optionally be characterized by measurements including, without limitation, western blot, marcomolecular mass determinations by biophysical determinations, SDS-PAGE/staining, HPLC and the like, antibody recognition assays, activity assays against various possible substrates illustratively including but not limited to VX, VR (N,N-diethy-2-(methyl-(2-methylpropoxy)phosphoryl)sulfanylethanamine), or VM N,N-diethyl-2-(methyl-(2-methylpropoxy)phosphoryl)sulfanylethanamin-e).

Also provided are isolated nucleic acids encoding the desired protein sequence analogues thereof, or fragments thereof. These nucleic acids can be used to produce the non-wild-type OPAAs of this invention. It is appreciated that as the nucleic acid code is well known, that one of ordinary skill in the art readily and immediately understands the nucleic acid sequence encoding a desired protein sequence. Thus, a description of a protein sequence is equally a description of an underlying nucleic acid sequence encoding the protein sequence.

The term "nucleotide" is intended to mean a base-sugar-phosphate combination either natural or synthetic, linear, circular and sequential arrays of nucleotides and nucleosides, e.g. cDNA, genomic DNA, mRNA, and RNA, oligonucleotides, oligonucleosides, and derivatives thereof. Included in this definition are modified nucleotides which include additions to the sugar-phosphate groups as well as to the bases.

The term "nucleic acid" or "polynucleotide" refers to multiple nucleotides attached in the form of a single or double stranded polynucleotide that can be natural, or derived synthetically, enzymatically, and by cloning methods. The term "oligonucleotide" refers to a polynucleotide of less than 200 nucleotides. The terms "nucleic acid" and "oligonucleotide" may be used interchangeably in this application.

A nucleic acid as used herein refers to single- or double-stranded molecules that may be DNA, including of the nucleotide bases A, T, C and G, or RNA, comprised of the bases A, U (substitutes for T), C, and G. The nucleic acid may represent a coding strand or its complement. Nucleic acid sequences as used herein are based upon the sequence naturally occurring, illustratively a sequence of SEQ ID NO: 3 of non-wild-type OPAA, or may include alternative codons that encode the same amino acid as that found in the naturally occurring sequence. Furthermore, nucleic acids may include codons that represent conservative substitutions of amino acids as are well known in the art.

The nucleic acid encoding the non-wild-type OPAA of this invention can be part of a recombinant nucleic acid construct comprising any combination of restriction sites and/or functional elements as are well known in the art that facilitate molecular cloning and other recombinant DNA manipulations. Thus, the present invention further provides a recombinant nucleic acid construct comprising a nucleic acid encoding a non-wild-type OPAA protein or peptide of this invention.

The present invention also provides a vector with a nucleic acid sequence encoding the inventive non-wild-type OPAA. Illustrative vectors include a plasmid, cosmid, cationic lipids, non-liposomal cationic vectors, cationic cyclodextrin, viruses with RNA or DNA genetic material, polyethylenimines, histidylated polylysine, or other vector system known in the art. A vector is optionally a plasmid. A suitable vector optionally possesses cell type specific expression or other regulatory sequences or sequences operable to stimulate or inhibit gene or protein expression. A vector illustratively contains a selection marker such as an antibiotic resistance gene.

The inventive nucleic acid sequence is optionally isolated from the cellular materials with which it is naturally associated. As used herein, the term "isolated nucleic acid" means a nucleic acid separated or substantially free from at least some of the other components of the naturally occurring organism, for example, the cell structural components commonly found associated with nucleic acids in a cellular environment and/or other nucleic acids. The isolation of nucleic acids is optionally accomplished by techniques such as cell lysis followed by phenol plus chloroform extraction, followed by ethanol precipitation of the nucleic acids. The nucleic acids of this invention can be isolated from cells according to methods well known in the art for isolating nucleic acids. Alternatively, the nucleic acids of the present invention can be synthesized according to standard protocols well described in the literature for synthesizing nucleic acids. Modifications to the nucleic acids of the invention are also contemplated, provided that the essential structure and function of the peptide encoded by the nucleic acid are maintained.

Numerous methods are known in the art for the synthesis and production of nucleic acid sequences illustratively including cloning and expression in cells such as *E. coli*, insect cells such as Sf9 cells, yeast, and mammalian cell types such as Hela cells, Chinese hamster ovary cells, or other cells systems known in the art as amendable to transfection and nucleic acid and/or protein expression. Methods of nucleic acid isolation are similarly recognized in the art. Illustratively, plasmid DNA amplified in *E. coli* is cleaved by suitable restriction enzymes such as NdeI and XhoI to linearize PA DNA. The PA DNA is subsequently isolated following gel electrophoresis using a S.N.A.P.™ UV-Free Gel Purification Kit (Invitrogen, Carisbad, Calif.) as per the manufacturer's instructions.

Numerous agents are amenable to facilitate cell transfection illustratively including synthetic or natural transfection agents such as LIPOFECTIN, baculovirus, naked plasmid or other DNA, or other systems known in the art.

The nucleic acid sequences of the invention may be isolated or amplified by conventional uses of polymerase chain reaction or cloning techniques such as those described in conventional texts. For example, the nucleic acid sequences of this invention may be prepared or isolated from DNA using DNA primers and PCR techniques. Alternatively, the inventive nucleic acid sequence may be obtained from gene banks derived from whole genomic DNA. These sequences, fragments thereof, modifications thereto and the full-length sequences may be constructed recombinantly using conventional genetic engineering or chemical synthesis techniques or PCR, and the like.

Recombinant or non-recombinant proteinase peptides or recombinant or non-recombinant proteinase inhibitor peptides or other non-peptide proteinase inhibitors can also be used in the present invention. Proteinase inhibitors are optionally modified to resist degradation, for example degradation by digestive enzymes and conditions. Techniques for the expression and purification of recombinant proteins are known in the art (see Sambrook Eds., Molecular Cloning: A Laboratory Manual 3rd ed. (Cold Spring Harbor, N.Y. 2001).

Some embodiments of the present invention are compositions containing a nucleic acid sequence that can be expressed as a peptide according to the invention. The engineering of DNA segment(s) for expression in a prokaryotic or eukaryotic system may be performed by techniques generally known to those of skill in recombinant expression. It is believed that virtually any expression system may be employed in the expression of the claimed nucleic acid and amino acid sequences.

As used herein, the terms "engineered" and "recombinant" cells are synonymous with "host" cells and are intended to refer to a cell into which an exogenous DNA segment or gene, such as a cDNA or gene encoding as non-wild-type OPAA has been introduced. Therefore, engineered cells are distinguishable from naturally occurring cells which do not contain a recombinantly introduced exogenous DNA segment or gene. A host cell is optionally a naturally occurring cell that is transformed with an exogenous DNA segment or gene or a cell that is not modified. Engineered cells are cells having a gene or genes introduced through the hand of man. Recombinant cells include those having an introduced cDNA or genomic DNA, and also include genes positioned adjacent to a promoter not naturally associated with the particular introduced gene.

To express a recombinant non-wild-type OPAA in accordance with the present invention one optionally prepares an expression vector that comprises a nucleic acid under the control of one or more promoters. To bring a coding sequence "under the control of" a promoter, one positions the 5' end of the translational initiation site of the reading frame generally between about 1 and 50 nucleotides "downstream" of (i.e., 3' of) the chosen promoter. The "upstream" promoter stimulates transcription of the inserted DNA and promotes expression of the encoded recombinant protein. This is the meaning of "recombinant expression" in the context used here.

Many standard techniques are available to construct expression vectors containing the appropriate nucleic acids and transcriptional/translational control sequences in order to achieve peptide expression in a variety of host-expression systems. Cell types available for expression include, but are not limited to, bacteria, such as *E. coli* and *B. subtilis* transformed with recombinant phage DNA, plasmid DNA or cosmid DNA expression vectors.

Certain examples of prokaryotic hosts are *E. coli* strain RR1, *E. coli* LE392, *E. coli* B. *E. coli*. chi. 1776 (ATCC No. 31537) as well as *E. coli* W3110 (F-, lambda-, prototrophic, ATCC No. 273325); bacilli such as *B. subtilis*; and other enterobacteriaceae such as *Salmonella typhimurium*, *Serratia marcescens*, and various *Pseudomonas* species.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is often transformed using pBR322, a plasmid derived from an *E. coli* species. Plasmid pBR322 contains genes for ampicillin and tetracycline resistance and thus provides easy means for identifying transformed cells. The pBR322 plasmid, or other microbial plasmid or phage must also contain, or be modified to contain, promoters that can be used by the microbial organism for expression of its own proteins. Another exemplary plasmid vector is the pSE420 vector that includes translation initiation sequences for optimal expression of mammalian genes in *E. coli*, and an ampicillin resistance gene for selection. The pSE420 vector also includes a lacO operator and lacI repressor for transcriptional regulation.

In addition, phage vectors containing replicon and control sequences that are compatible with the host microorganism can be used as transforming vectors in connection with these hosts. For example, the phage lambda may be utilized in making a recombinant phage vector that can be used to transform host cells, such as *E. coli* LE392.

Further useful vectors include pIN vectors and pGEX vectors, for use in generating glutathione S-transferase (GST) soluble fusion proteins for later purification and separation or cleavage. Other suitable fusion proteins are those with β-galactosidase, ubiquitin, or the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

It is contemplated that the nucleic acids of the disclosure may be "overexpressed", i.e., expressed in increased levels relative to its natural expression in cells of its indigenous organism, or even relative to the expression of other proteins in the recombinant host cell. Such overexpression may be assessed by a variety of methods, including radio-labeling and/or protein purification. However, simple and direct methods are preferred, for example, those involving SDS/PAGE and protein staining or immunoblotting, followed by quantitative analyses, such as densitometric scanning of the resultant gel or blot. A specific increase in the level of the recombinant protein or peptide in comparison to the level in natural human cells is indicative of overexpression, as is a relative abundance of the specific protein in relation to the other proteins produced by the host cell and, e.g., visible on a gel.

A nucleic acid of this invention can be in a cell, which can be a cell expressing the nucleic acid whereby a peptide of this invention is produced in the cell. In addition, the vector of this invention can be in a cell, which can be a cell expressing the nucleic acid of the vector whereby a peptide of this invention is produced in the cell. It is also contemplated that the nucleic acids and/or vectors of this invention can be present in a host animal (e.g., a transgenic animal) which expresses the nucleic acids of this invention and produces the peptides of this invention.

The nucleic acid encoding the non-wild-type OPAA of this invention can be any nucleic acid that functionally encodes the non-wild-type OPAA. To functionally encode the peptides (i.e., allow the nucleic acids to be expressed), the nucleic acid of this invention can include, for example, expression control sequences, such as an origin of replication, a promoter, an enhancer and necessary information processing sites, such as ribosome binding sites, RNA splice sites, polyadenylation sites and transcriptional terminator sequences.

The nucleic acid sequences encode the non-wild-type OPAA of this invention as SEQ ID NO: 2, 3, and 4. Preferably, the nucleic acid sequences are cloned into the NcoI and EcoRI sites of a pSE420 expression vector. The cloned gene translates to a polypeptide that lacks the last 77 carboxyl-terminus amino acids of the OPAA enzyme. The OPAA enzyme with the desired mutations is constructed by site-directed mutagenesis.

Method of Use

It is further contemplated that a non-wild-type OPAA may be provided for pharmaceutical use. Pharmaceutical compositions optionally include effective amounts of non-wild-type OPAA, or derivative products, together with pharmaceutically acceptable diluents, preservatives, solubilizers, emulsifiers, adjuvants and/or carriers needed for administration. (See PCT 97/01331 for an exemplary listing) The optimal pharmaceutical formulation for a desired biologically active agent will be determined by one skilled in the art depending upon the route of administration and desired dosage. Exemplary pharmaceutical compositions are disclosed in Remington's Pharmaceutical Sciences (Mack Publishing Co., 18th Ed., Easton, Pa., pgs. 1435-1712 (1990)). The pharmaceutical compositions of the present invention may be administered by oral and non-oral preparations (e.g., intramuscular, subcutaneous, transdermal, visceral, IV (intravenous), IP (intraperitoneal), intraarticular, placement in the ear, ICV (intracerebralventricular), intraarterial, intrathecal, intracapsular, intraorbital, injectable, pulmonary, nasal, rectal, and uterine-transmucosal preparations).

The non-wild-type OPAA may be delivered as naked polypeptide, in aqueous solution, in an emulsion, or in other suitable delivery composition. In some embodiments, the invention is delivered as a component of a pharmaceutical package. Alternatively, a protein (or multiple proteins) is present in an emulsion including one or more emulsification agents. In some embodiments, a non-wild-type OPAA is emulsified. Suitable emulsification agents illustratively include supramolecular biovectors (SMBV), nanoparticles such as described by Major, M. et al, Biochim. Biophys. Acta, 1997; 1327:32-40, De Migel, I, et al, Pharm. Res., 2000; 17:817-824, U.S. Pat. Nos. 6,017,513, 7,097,849, 7,041,705, 6,979,456, 6,846,917, 6,663,861, 6,544,646, 6,541,030, 6,368,602, Castignolles, N., et el, Vaccine, 1996; 14:1353-1360, Prieur, E., et al, Vaccine, 1996; 14:511-520, Baudner B, et al, Infect Immun, 2002; 70:4785-4790; Liposomes such as described by El Guink et al., Vaccine, 1989; 7:147-151, and in U.S. Pat. No. 4,196,191; or other agents known in the art. Agents suitable for use are generally available from Sigma-Aldrich, St. Louis, Mo. The emulsification agent is optionally a dimethyl dioctadecyl-ammonium bromide. Optionally the adjuvant is monophosphoryl lipid A.

Suitable pharmaceutically acceptable carriers facilitate administration of the non-wild-type OPAA are physiologically inert and/or nonharmful. Carriers may be selected by one of skill in the art. Exemplary carriers include sterile water or saline, lactose, sucrose, calcium phosphate, gelatin, dextran, agar, pectin, peanut oil, olive oil, sesame oil, and water. Additionally, the carrier or diluent may include a time delay material, such as glycerol monostearate or glycerol distearate alone or with a wax. In addition, slow release polymer formulations can be used.

The inventive composition may also contain conventional pharmaceutical ingredients, such as preservatives, or chemical stabilizers. Suitable ingredients operable herein include, for example, casamino acids, sucrose, gelatin, phenol red, N-Z amine, monopotassium diphosphate, lactose, lactalbumin hydrolysate, and dried milk.

Suitable methods of administration of a non-wild-type OPAA include, but are not limited to intramuscular, intravenous, intranasal, mucosal, oral, parenteral, intravaginal, transdermal, via aerosol delivery or by any route that produces the desired biological effect.

A non-wild-type OPAA protein of the invention may be packaged in a single dosage for administration by parenteral (i.e., intramuscular, intradermal or subcutaneous) or nasopharyngeal (i.e., intranasal) administration. The non-wild-type OPAA may also be delivered by inhalation. Alternatively, the non-wild-type OPAA is combined with a pharmaceutically acceptable carrier to facilitate administration. The carrier is usually water or a buffered saline, with or without a preservative. The non-wild-type OPAA may be lyophilized for resuspension at the time of administration or in solution.

The inventive non-wild-type OPAA may be microencapsulated to provide a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that may be considered. Examples of useful polymers illustratively include polycarbonates, polyesters, polyurethanes, polyorthoesters polyamides, poly (d,l-lactide-co-glycolide) (PLGA) and other biodegradable polymers.

The inventive non-wild-type OPAA may additionally contain stabilizers such as thimerosal (ethyl(2-mercaptobenzoate-S)mercury sodium salt) (Sigma Chemical Company, St. Louis, Mo.) or physiologically acceptable preservatives.

Further, an effective amount of a non-wild-type OPAA of the invention may be administered so that a human or other animal who are exposed to a toxin, illustratively VX, by administering an "effective amount" is of between about 0.05 to about 1000 µg/mL of the non-wild-type OPAA. A suitable dosage is about 1.0 mL of such an effective amount. Such a composition may be administered 1-3 times per day over a 1 day to 12 week period. However, suitable dosage adjustments may be made by the attending physician or veterinarian depending upon the age, sex, weight and general health of the subject. Such a composition may be administered parenterally, optionally intramuscularly or subcutaneously. However, the composition may also be formulated to be administered by any other suitable route, including orally or topically.

As used herein, the terms "subject" or "organism" are treated synonymously and are defined as any being that includes a gene, including a virus. A subject illustratively includes: a mammal including humans, non-human primates, horses, goats, cows, sheep, pigs, dogs, cats, and rodents; arthropods; single celled organisms illustratively bacteria; viruses; and cells.

In some embodiments, a process of decontaminating a surface is provided. Such processes include applying the non-wild-type OPAA to a surface is contaminated with one or more toxins, illustratively VX. Any delivery mechanism for decontaminating a surface with non-wild-type OPAA is operable including spraying, immersing, or other contact mechanism. The non-wild-type OPAA may be delivered in any form described above, preferably as an aqueous solution. For testing the contaminated surfaces, the non-wild-type OPAA is maintained in contact with the surface for a contact period sufficient to catalyze degradation, optionally complete degradation, of the toxin present on the surface.

In some embodiments, the invention provides regimens or kits comprising one or more of the following in a package or container. (1) a pharmacologically active composition comprising a pharmaceutically acceptable carrier and the inventive, non-wild-type OPAA or its variant, derivative or structural equivalent thereof; (2) an additional boosting agent; and (3) apparatus or applicator to administer the pharmaceutically active composition to the subject, such as a syringe, nebulizer, etc.

When a kit is supplied, the different components of the composition may be packaged in separate containers. If appropriate, and admixed immediately before use. Such packaging of the components separately may permit long-term storage without losing the active components function.

The reagents included in the kits can be supplied in containers of any sort such at the life of the different components are preserved and are not adsorbed or altered by the materials of the container. For example, sealed glass ampules may contain lyophilized non-wild-type OPAA and variants, derivatives and structural equivalents thereof, or buffers that have been packaged under a neutral, non-reacting gas, such as nitrogen. Ampules may consist of any suitable material, such as glass, organic polymers, such polycarbonate, polystyrene, etc., ceramic, metal or any other material typically employed to hold similar regents. Other examples of suitable containers include simple bottles that may be fabricated from similar substances as ampules, and envelopes, that may comprise foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other container may have two compartments that are separated by a readily removable membrane that upon removal permits the components to be mixed. Removable membranes may be glass, plastic, rubber, etc.

Kits may also be supplied with instructional materials that describes a method for combining and administering the components. Instructions may be printed on paper or other substrate, and/or may be supplied as an electronic-readable medium, such as a floppy disc, CD-ROM, DVD-ROM, Zip disc, videotape, audiotape, flash memory device etc. Detailed instructions may not be physically associated with the kit; instead, a user may be directed to an internet web site specified by the manufacturer or distributer of the kit, or supplied as electronic mail.

EXPERIMENT

OPAA Expression Vector and Site-Directed Mutagenesis of the OPAA Gene

The gene encoding the OPAA enzyme was originally cloned from *Alteromonas* sp. JD6.5, as described. The present gene was modified by site-directed mutagenesis, lacks the last 77 carboxyl-terminus amino acids of the OPAA enzyme. This truncated gene was cloned into the NcoI and the EcoRI sites of the pSE420 expression vector of *E. coli*. The resulting mutant plasmids were introduced into *E. coli* BL21 (DE3) competent cells by electroporation and were grown to late log phase in 1 liter flasks without induction to produce enzyme. The complete coding regions for the mutant OPAA was sequenced by DNA2.0 (www.dna20.com).

Production and Purification of Engineered OPAAs

The engineered OPAA enzymes were prepared by a method similar to that described previously is U.S. Pat. No. 9,017,982, which is incorporated herein by reference. Briefly, an *E. coli* DH5a culture containing the OPAA containing the pSE420 plasmid was grown at 37° C. in 10 L of LB containing 0.1 mg/mL ampicillin and 0.1 mM $MnCl_2$. Cells were grown to mid-log phase (A600=0.5) and induced with 1 mM IPTG. After four hours of induction, the cells were harvested by centrifugation. After the centrifugation, proteins from the supernatant were precipitated in 65% ammonium sulfate. This pellet was resuspended in 13 mL of 10 mM bis-tris-propane, pH 8.0 with 0.1 mM $MnCl_2$ and passed through a size exclusion column. The active fractions were pooled and loaded on a 10 ml Q Sepharose column and eluted with a 0.2-0.6 M NaCl gradient. The active fractions from the Q Sepharose column were pooled, precipitated in 65% ammonium sulfate, resuspended in and dialyzed against 10 mM bis-tris-propane, pH 8.0 with 0.1 mM $MnCl_2$. The resulting protein migrated with apparent homogeneity on SDS-PAGE.

VX Enzymatic Assay

The enzymatic assay measured the concentration of free thiol from the enzyme-catalyzed cleavage of the P—S bond of the V-agents. For example, VX samples were Chemical Agent Standard Analytical Reference Material (CASARM), obtained from Edgewood Chemical Biological Center Stocks, and were of the highest purity available, typically 99.9+/−5.4 weight % by oxidation-reduction titration, traceable to National Institute of Standards and Technology through 0.1 N iodine solution SRM 136e. The kinetic constants were determined by spectrophotometry using 0.3 mM DTNB) in 50 mM bis-tris-propane buffer, pH 8.0 and 0.1 mM $MnCl_2$ at 25° C. in a 1 mL cuvette with a total sample volume of 0.5 mL. A wild-type sample and a sample containing mutations at positions 212, 215 and 342 were monitored at 412 nm for five minutes and activity was calculated using an extinction coefficient of 14,150 $M^{-1}$ $cm^{-1}$.

Kinetic parameters were calculated using Biosoft EnzFitter® software (Biosoftcom). Activity data were generally collected at substrate concentrations ranging from ⅓ to three times the Km under conditions that consumed less than 10% of the substrate. At least five different substrate concentrations were used for each determination.

Tables 1-2 illustrate the increased catalytic efficiency of the FLYA OPAA mutant enzyme on VX and VR, respectively. Tables 3-5 illustrate the increased catalytic efficiency of the FLYG OPAA mutant enzyme on VX, VR and CVX, respectively. Tables 5-6 illustrate the increased catalytic efficiency of the FLYD-Q OPAA mutant enzyme on VM and CVX, respectively.

TABLE 1

Kinetic Parameters of wild-type (WT) and FLYA OPAA enzyme on VX.

| Enzyme | $k_{cat}$ (min$^{-1}$) | $K_m$ (M$^{-1}$) | $k_{cat}/K_m$ (min$^{-1}$ M$^{-1}$) |
|---|---|---|---|
| Wild-type (WT) OPAA | 0.49 | 2028.45 | 2.41E+02 |
| Mutated OPAA (FLYA) | 17.57 | 6648.29 | 2.64E+03 |

TABLE 2

Kinetic Parameters of wild-type (WT) and FLYA OPAA enzyme on VR

| Enzyme | $k_{cat}$ (min$^{-1}$) | $K_m$ (M$^{-1}$) | $k_{cat}/K_m$ (min$^{-1}$ M$^{-1}$) |
| --- | --- | --- | --- |
| Wild-type (WT) OPAA | 1.80 | 3279.77 | 5.48E+02 |
| Mutated OPAA (FLYA) | 8.98 | 499.59 | 1.80E+04 |

TABLE 3

Kinetic Parameters of wild-type (WT) and FLYG OPAA enzyme on VX.

| Enzyme | $k_{cat}$ (min$^{-1}$) | $K_m$ (M$^{-1}$) | $k_{cat}/K_m$ (min$^{-1}$ M$^{-1}$) |
| --- | --- | --- | --- |
| Wild-type (WT) OPAA | 0.49 | 2028.45 | 2.41E+02 |
| Mutated OPAA (FLYG) | 19.05 | 4321.06 | 4.41E+03 |

TABLE 4

Kinetic Parameters of wild-type (WT) and FLYG OPAA enzyme on VR.

| Enzyme | $k_{cat}$ (min$^{-1}$) | $K_m$ (M$^{-1}$) | $k_{cat}/K_m$ (min$^{-1}$ M$^{-1}$) |
| --- | --- | --- | --- |
| Wild-type (WT) OPAA | 1.80 | 3279.77 | 548E+02 |
| Mutated OPAA (FLYG) | 51.09 | 4675 | 1.09E+04 |

TABLE 5

Kinetic Parameters of wild-type (WT) and FLYG OPAA enzyme on CVX.

| Enzyme | $k_{cat}$ (min$^{-1}$) | $K_m$ (M$^{-1}$) | $k_{cat}/K_m$ (min$^{-1}$ M$^{-1}$) |
| --- | --- | --- | --- |
| Wild-type (WT) OPAA | 2.36 | 1700 | 1.39E+03 |
| Mutated OPAA (FLYG) | 46.35 | 6906.96 | 6.71E+03 |

TABLE 6

Kinetic Parameters of wild-type (WT) and FLYD-Q OPAA enzyme on VM.

| Enzyme | $k_{cat}$ (min$^{-1}$) | $K_m$ (M$^{-1}$) | $k_{cat}/K_m$ (min$^{-1}$ M$^{-1}$) |
| --- | --- | --- | --- |
| Wild-type (WT) OPAA | 0.412 | 6900 | 59.8 |
| Mutated OPAA (FLYD-Q) | 9.56 | 9800 | 975 |

TABLE 7

Kinetic Parameters of wild-type (WT) and FLYD-Q OPAA enzyme on CVX.

| Enzyme | $k_{cat}$ (min$^{-1}$) | $K_m$ (M$^{-1}$) | $k_{cat}/K_m$ (min$^{-1}$ M$^{-1}$) |
| --- | --- | --- | --- |
| Wild-type (WT) OPAA | 2.36 | 1700 | 1390 |
| Mutated OPAA (FLYD-Q) | 10.1 | 4200 | 2400 |

The foregoing description of the specific embodiments will so fully reveal the general nature of the embodiments herein that others may, by applying current knowledge, readily modify and/or adapt for various applications such specific embodiments without departing from the general concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein may be practiced with modification within the spirit and scope of the appended claims.

---

The invention claimed is:

1. A mutant organophosphorus acid anhydrolase (OPAA) enzyme, wherein said anhydrolase comprises an amino acid sequence having at least 90% sequence identity to SEQ ID NO: 1, and a non-wild-type amino acid corresponding to each of positions 212, 215, 342, and 343 of SEQ ID NO: 1.

2. The mutant OPAA of claim 1, wherein said non-wild-type amino acid at sequence position 212 of SEQ ID NO: 1 is phenylalanine (F).

3. The mutant OPAA of claim 1, wherein said non-wild-type amino acid at sequence position 342 of SEQ ID NO: 1 is leucine (L).

4. The mutant OPAA of claim 1, wherein said non-wild-type amino acid at sequence position 215 of SEQ ID NO: 1 is tyrosine (Y).

5. The mutant OPAA of claim 1, wherein said non-wild-type amino acid at sequence position 343 of SEQ ID NO: 1 is alanine (A).

6. The mutant OPAA of claim 1, wherein said non-wild-type amino acid at sequence position 343 of SEQ ID NO: 1 is glycine (G).

7. The mutant OPAA of claim 1, wherein said non-wild-type amino acid at sequence position 343 of SEQ ID NO: 1 is aspartic acid (D).

8. The mutant OPAA of claim 1, wherein said OPAA comprises the amino acid sequence of SEQ ID NO: 2.

9. The mutant OPAA of claim 1, wherein said OPAA comprises the amino acid sequence of SEQ ID NO: 3.

10. The mutant OPAA of claim 1, further comprising a non-wild-type amino acid at sequence position 332 of SEQ ID NO: 1.

11. The mutant OPAA of claim 10, wherein said non-wild-type amino acid at sequence position 332 of SEQ ID NO: 1 is glutamine (Q).

12. The mutant OPAA of claim 10, wherein said OPAA comprises the amino acid sequence of SEQ ID NO: 4.

13. The mutant OPAA of claim 1, wherein said OPAA comprises phenylalanine (F) at sequence position 212, leucine (L) at sequence position 342, tyrosine (Y) at sequence position 215, and alanine (A) at sequence position 343 of SEQ ID NO: 1.

14. The mutant OPAA of claim 1, wherein said OPAA comprises phenylalanine (F) at sequence position 212, leucine (L) at sequence position 342, tyrosine (Y) at sequence position 215, and glycine (G) at sequence position 343 of SEQ ID NO: 1.

15. The mutant OPAA of claim 10, wherein said OPAA comprises phenylalanine (F) at sequence position 212, leucine (L) at sequence position 342, tyrosine (Y) at sequence position 215, aspartic acid (D) at sequence position 343, and glutamine (Q) at sequence position 332 of SEQ ID NO: 1.

16. A method of degrading V-agents Ethyl ({2-[bis(propan-2-yl)amino]ethyl}sulfanyl)(methyl)phosphinate (VX) and/or N,N-diethyl-2-(methyl-(2-methylpropoxy)phosphoryl)sulfanylethanamine) (VR), comprising contacting VX and/or VR with a mutant organophosphorus acid anhydrolase enzyme, wherein said OPAA enzyme comprises the amino acid sequence of SEQ ID NO: 2.

17. A method of degrading V-agents VX, VR and/or S-[2-(Diethylamino)ethyl] O-n-butyl methylphosphonothioate) (CVX), comprising contacting VX, VR and/or CVX with a mutant organophosphorus acid anhydrolase enzyme, wherein said OPAA enzyme comprises the amino acid sequence of SEQ ID NO: 3.

18. A method of degrading V-agents (S-[2-(Diethylamino)ethyl] O-ethyl methylphosphonothioate) (VM) and/or CVX, comprising contacting VM and/or CVX with a mutant organophosphorus acid anhydrolase enzyme, wherein said OPAA enzyme comprises the amino acid sequence of SEQ ID NO: 4.

19. A kit for degrading VX and/or VR, comprising:
(a) a mutant organophosphorus acid anhydrolase, wherein said anhydrolase comprises the amino acid sequence of SEQ ID NO: 2; and
(b) a pharmaceutically-acceptable carrier.

20. A kit for degrading VX, VR and/or CVX comprising:
(a) a mutant organophosphorus acid anhydrolase, wherein said anhydrolase comprises the amino acid sequence of SED ID NO: 3; and
(b) a pharmaceutically-acceptable carrier.

21. A kit for degrading VM and/or CVX comprising:
(a) a mutant organophosphorus acid anhydrolase, wherein said anhydrolase comprises the amino acid sequence of SED ID NO: 4; and
(b) a pharmaceutically-acceptable carrier.

* * * * *